(12) United States Patent
Onishi

(10) Patent No.: US 7,575,554 B2
(45) Date of Patent: Aug. 18, 2009

(54) BREATHING MONITORING DEVICE HAVING A MULTI-POINT DETECTOR

(75) Inventor: Hiroshi Onishi, Yamanashi (JP)

(73) Assignee: University of Yamanashi, Kofu-shi (JP)

( * ) Notice: Subject to any disclaimer, the term of this patent is extended or adjusted under 35 U.S.C. 154(b) by 23 days.

(21) Appl. No.: 11/902,440

(22) Filed: Sep. 21, 2007

(65) Prior Publication Data

US 2009/0082687 A1 Mar. 26, 2009

(51) Int. Cl.
*A61B 5/08* (2006.01)
*A61B 5/103* (2006.01)

(52) U.S. Cl. .................. 600/534; 600/587; 600/595

(58) Field of Classification Search ............. 600/534, 600/595

See application file for complete search history.

(56) References Cited

U.S. PATENT DOCUMENTS

2004/0210155 A1* 10/2004 Takemura et al. ........... 600/534
2004/0243005 A1* 12/2004 Rapps ....................... 600/481
2004/0254492 A1* 12/2004 Zhang et al. ............... 600/538
2007/0032748 A1* 2/2007 McNeil et al. .............. 600/595
2007/0173684 A1* 7/2007 Elliott ....................... 600/27

* cited by examiner

*Primary Examiner*—Charles A Marmor, II
*Assistant Examiner*—Christian Y Jang
(74) *Attorney, Agent, or Firm*—Oliff & Berridge, PLC

(57) ABSTRACT

In medical situation, a self breathing holding method using no breathing monitoring device shows inferior accuracy in holding breathing by a patient with poor understanding of the self breathing holding method. In view of the above, development of a readily understandable breathing holding method and breathing monitoring device with high accuracy has been desired. A breathing monitoring device having a multi-point detector comprises a housing mounted to a treatment couch for a patient to lie thereon, so as to cover the patient's body, such as a chest, an abdomen, or the like; a displacement amount determination unit mounted to the housing, for determining displacement amounts of at least two points on the patient's chest and abdomen; and a respiration level determination unit for determining a combined displacement amount which is a combination of the displacement amounts determined of the patient's chest and abdomen due to respiration.

8 Claims, 9 Drawing Sheets

BREATHING MONITORING DEVICE HAVING A MULTI-POINT DETECTOR

BACKGROUND OF THE INVENTION

1. Field of the Invention

The present invention relates to a breathing monitoring device having a multi-point detector for monitoring the movement of the chest due to chest breathing and the movement of the abdomen due to abdominal breathing, using a determination means for determining a movement amount, mounted on a plurality of portions on a patient's body, which physically move due to respiration, to achieve highly accurate monitoring of a combined displacement amount of the patient's body due to respiration.

2. Description of the Related Art

In radio-therapy irradiation to or image capturing of a patient's body, using a CT (computer tomography system) device or a radio therapy system, the patient's target portion may remain unstable in position due to physical movement of his/her body due to respiration. This leads to a problem including deterioration in quality of a captured image, irradiation to normal tissues other than the treatment target portion, and so forth. In view of the above, conventionally, a so-called respiratory-gated technique (synchronization with respiration) is applied to electrically determine the amount of movement of the patient's body, using laser or infra-red radiation and to carry out image capturing and/or radio-therapy irradiation, using a signal in synchronism with the body movement.

However, according to a conventional respiration-gated technique, in which laser or infra-red radiation is applied to only one of the patient's chest and abdomen in determining the movement of his/her body, only either one of the lung and abdominal breathings can be subjected to determination. Moreover, determination of respiration-caused movement by means of laser or infra-red radiation uses a laser, an infra-red radiation sensor, or an electrical sensor, and also a calculation computer and an analogue circuit for signal processing the respiration-caused movement amount. This results in the device complicated and expensive.

In radio-therapy irradiation applied relative to a chest or an abdomen, for example, the patient is required to hold breathing for the purpose of reducing a PTV (or planning target volume), with various breathing holding methods available, and the irradiation is applied while monitoring the patient's respiration. However, as the monitoring relies on the information concerning only one of the chest and the abdomen, the ventilation amount in free breathing, in which abdominal breathing and chest breathing coexist, and the exact tumor position are not accurately reflected.

In a medical situation, a self breathing holding method using no breathing monitoring device is conventionally employed. However, review on the self breathing holding method shows extremely inferior accuracy in holding breathing by a patient with poor understanding of the self breathing holding method. In view of the above, development of a readily understandable breathing holding method and breathing monitoring device with high accuracy has been desired.

SUMMARY OF THE INVENTION

According to the present invention, there is provided a breathing monitoring device having a multi-point detector, comprising a housing mounted to a treatment couch for a patient to lie thereon, so as to cover the patient's body, such as a chest, an abdomen, or the like; displacement amount determination means mounted to the housing, for determining displacement amounts of at least two points on the patient's chest and abdomen; and respiration level determination means for determining a combined displacement amount which is a combination of the displacement amounts determined of the patient's chest and abdomen due to respiration.

In one embodiment of the present invention, the displacement amount determination means for determining displacement amounts of at least two points on the patient's chest and abdomen may comprise contact-type determination means having a probe attached to a tip end thereof or non-contact-type determination means utilizing optic, magnetic, supersonic, or the like.

In another embodiment of the present invention, the contact-type determination means having a probe attached to a tip end thereof may have probes for abutting on at least two points on the chest and the abdomen, respectively; a connection arm connecting the probes; a support arm for supporting the connection arm at a center thereof so as to rock and a displacement amount indicator extending from an axially attached point of the support arm in a direction opposite the support arm.

In still another embodiment of the present invention, the contact-type determination means having a probe attached to the tip end thereof may have two probes for abutting on at least two points on the chest and the abdomen, respectively, and one long arm and one short arms for respectively supporting the probes, and an operation of each of the arms may be transformed into an angular change of a displacement amount indicator by utilizing a pulley and a wire.

In yet another embodiment of the present invention, the patient may visually recognize the combined displacement amount of the patient's body due to respiration, and controls by himself/herself such that the combined displacement amount of the patient's body due to respiration stays in a specific range.

In yet another embodiment of the present invention, the breathing monitoring device having a multi-point detector may further comprise an electric signal generation mechanism for notifying a technical staff remote treating the patient when the patient visually recognizes the combined displacement amount of the patient's body due to respiration and recognizes that the combined displacement amount of the patient's body due to respiration stays in a specific range.

In yet another embodiment of the present invention, the breathing monitoring device having a multi-point detector may further comprise a signal generation mechanism for generating a synchronizing signal for controlling an inspection device and/or a treatment device so as to suspend or continue an inspection and/or treatment operation when the patient visually recognizes the combined displacement amount of the patient's body due to respiration and recognizes that the combined displacement amount of the patient's body due to respiration stays in a specific range.

According to the present invention, determination of the movement of the patient's body due to respiration is made by simply combining the displacement amounts of a plurality of portions of the patient's body. With this arrangement, a respiration level indicator can indicate a value in accordance with the combined displacement amount of the patient's body due to respiration. This enables highly accurate respiration-gated detection. Moreover, as the entire device is composed mechanically, an inexpensive device free from an electric circuit can be made. The simple structure of the device ensures readily maintenance with suppressed running costs.

DESCRIPTION OF THE PREFERRED EMBODIMENTS

The present invention has been conceived in order to address the above described problem, and to make possible accurate determination of a combined displacement amount of the patient's body due to respiration to enable the patient to visually recognize the combined displacement amount of his/her body due to respiration and to simultaneously send a respiration synchronism signal to an inspection device and/or a treatment device. In the following, embodiments of the breathing monitoring device having a multi-point detector according to the present invention will be described with reference to the following drawings.

Figure 1:
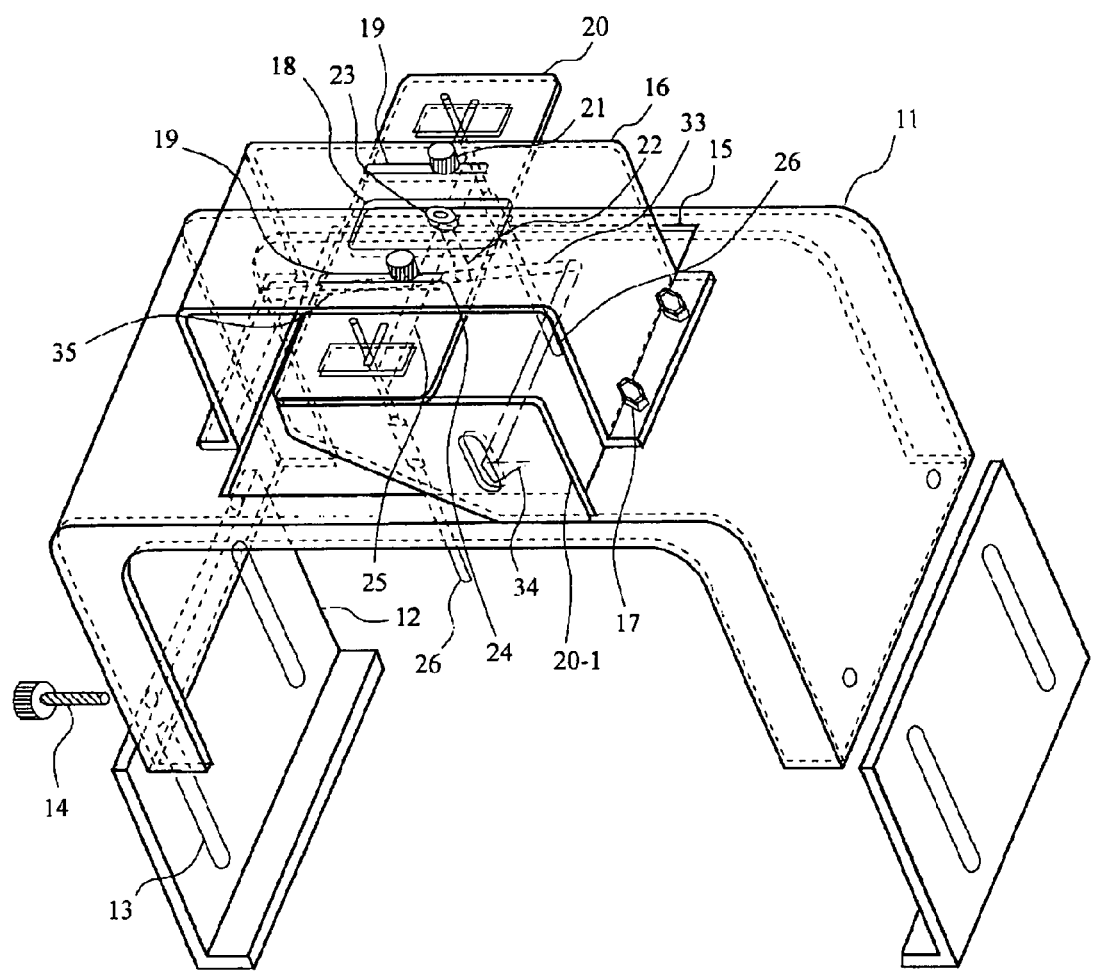
FIG. 1 is a perspective view showing a complete breathing monitoring device having a multi-point detector according to a first embodiment of the present invention.
Figure 2:
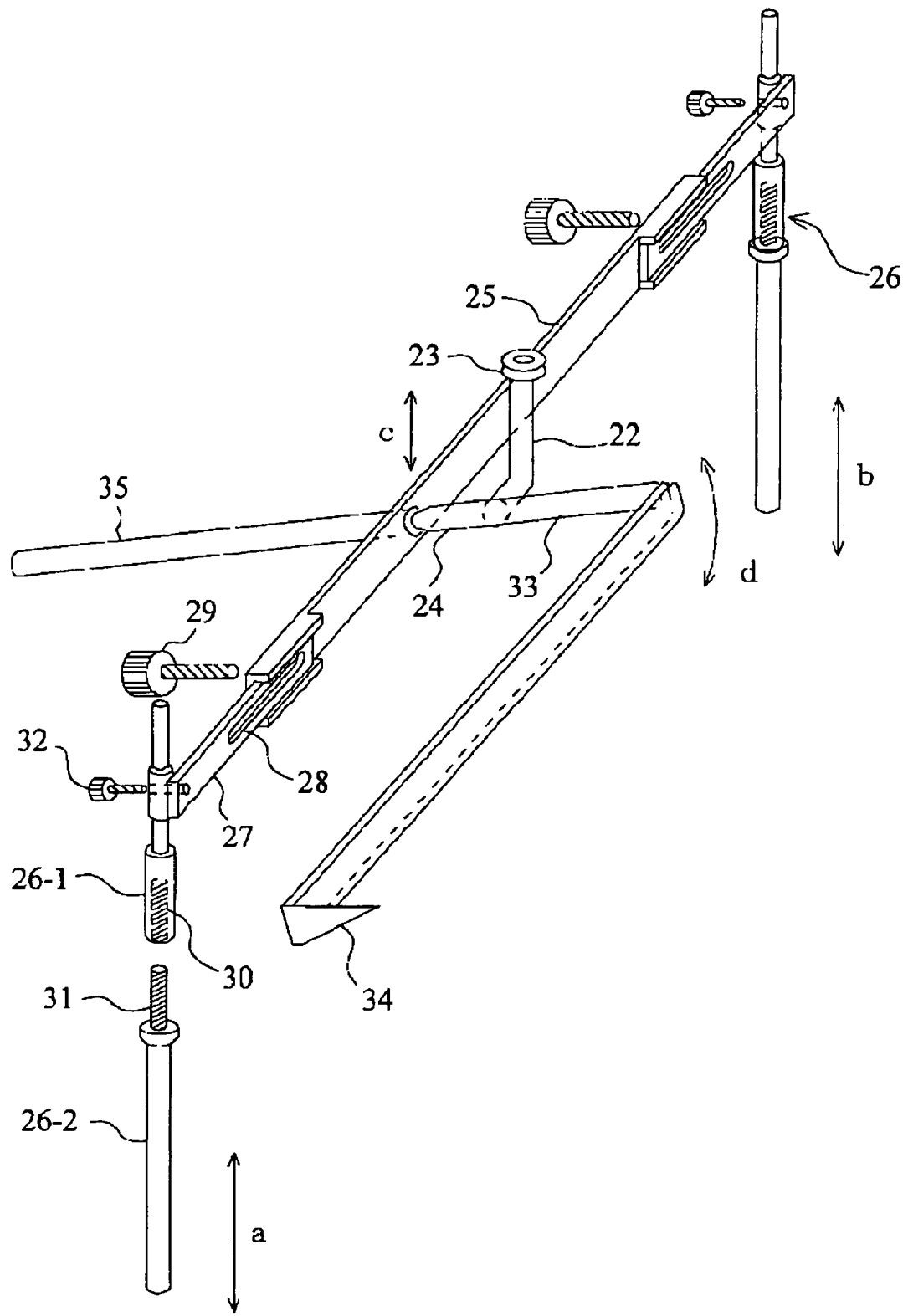
FIG. 2 is a perspective view showing elements of the breathing monitoring device having a multi-point detector.
Figure 3:
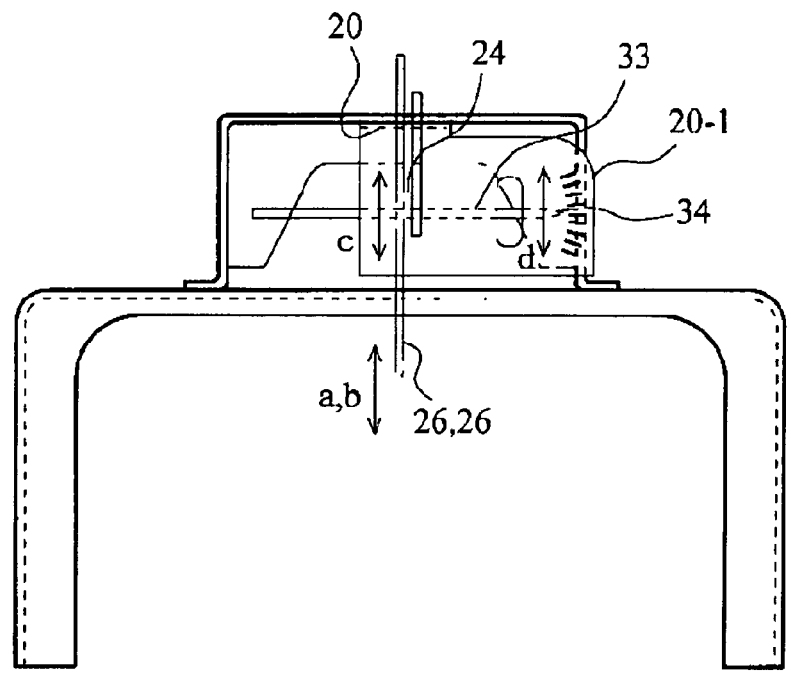
FIG. 3 is a front view schematically showing the breathing monitoring device having a multi-point detector.
Figure 4:
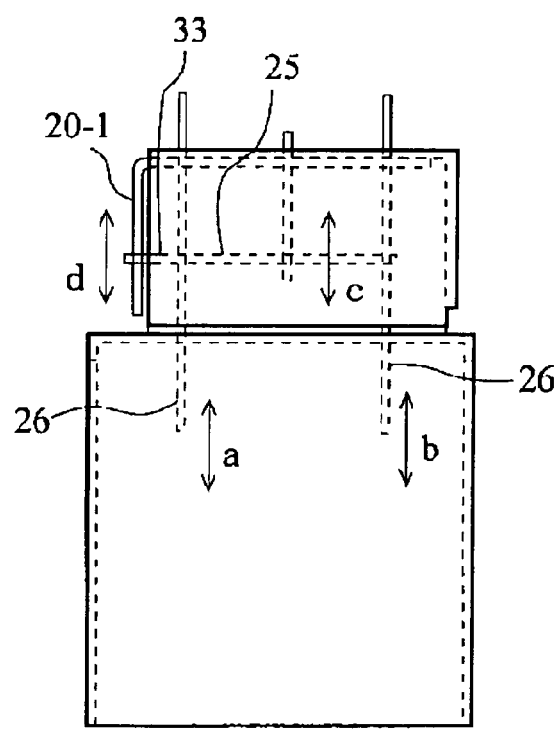
FIG. 4 is a side view showing the breathing monitoring device having a multi-point detector.
Figure 5:
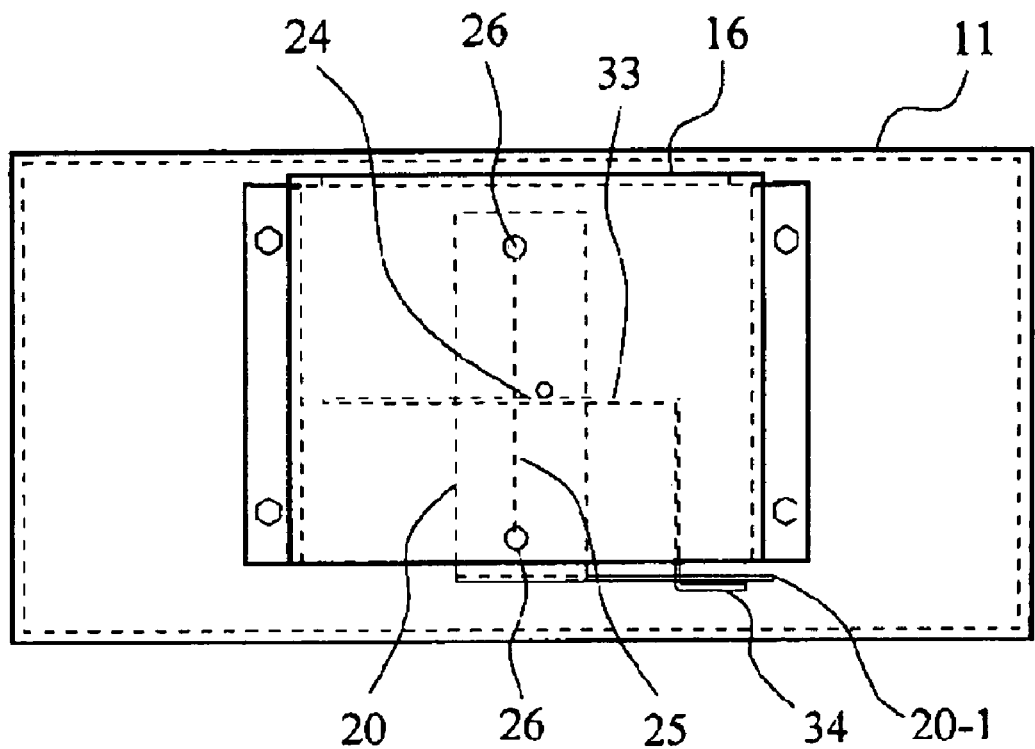
FIG. 5 is a plan view showing the breathing monitoring device having a multi-point detector.
Figure 6:
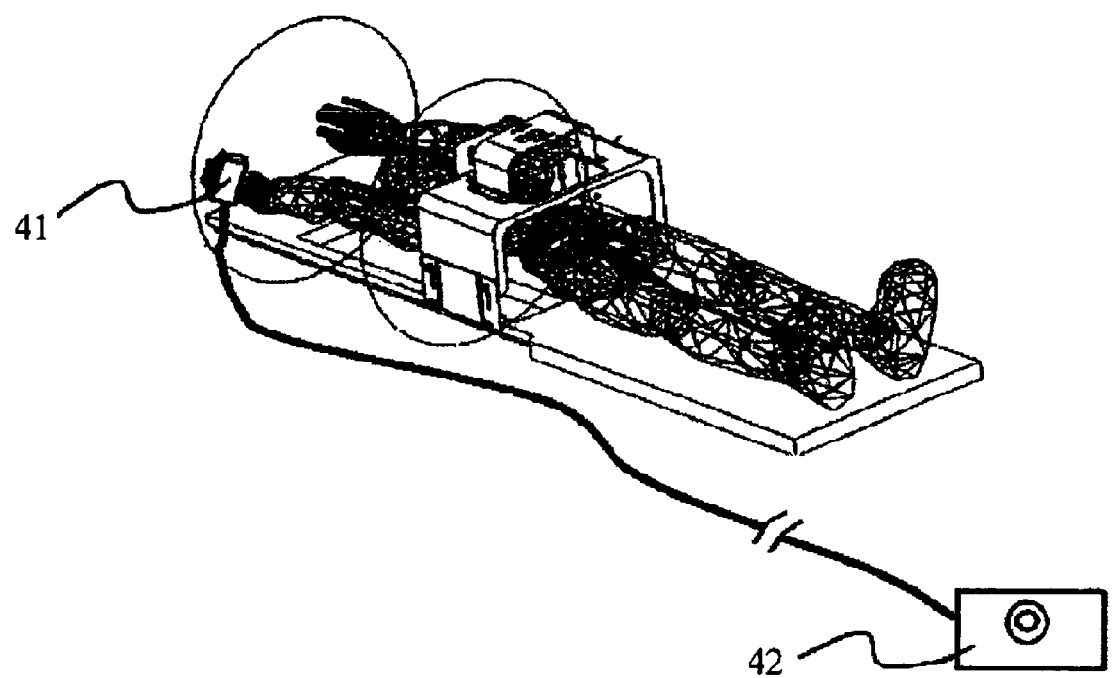
FIG. 6 is a diagram schematically showing the breathing monitoring device having a multi-point detector mounted to a treatment couch, with a patient lying thereon.
Figure 7:
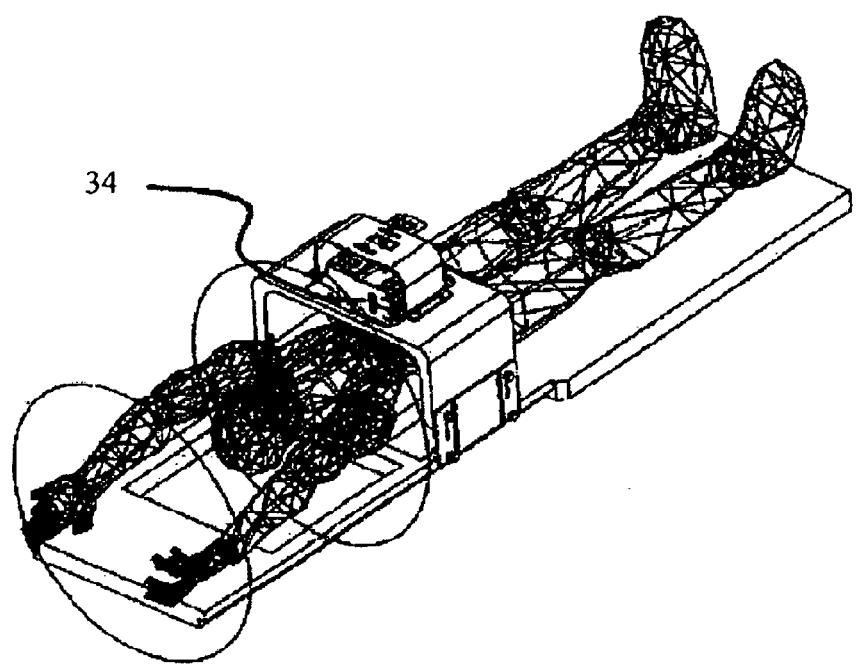
FIG. 7 is a diagram schematically showing the breathing monitoring device having a multi-point detector in use, viewed from the head of the patient.

FIG. 1 is a perspective view showing a complete breathing monitoring device having a multi-point detector according to a first embodiment of the present invention; FIG. 2 is a perspective view showing elements thereof; FIG. 3 is a front view schematically showing the breathing monitoring device having a multi-point detector; FIG. 4 is a side view thereof; FIG. 5 is a plan view thereof; FIG. 6 is a diagram schematically showing the breathing monitoring device having a multi-point detector mounted to a treatment couch, with a patient lying thereon; and FIG. 7 is a diagram schematically showing the breathing monitoring device having a multi-point detector in use, viewed from the head of the patient.

Figure 8:
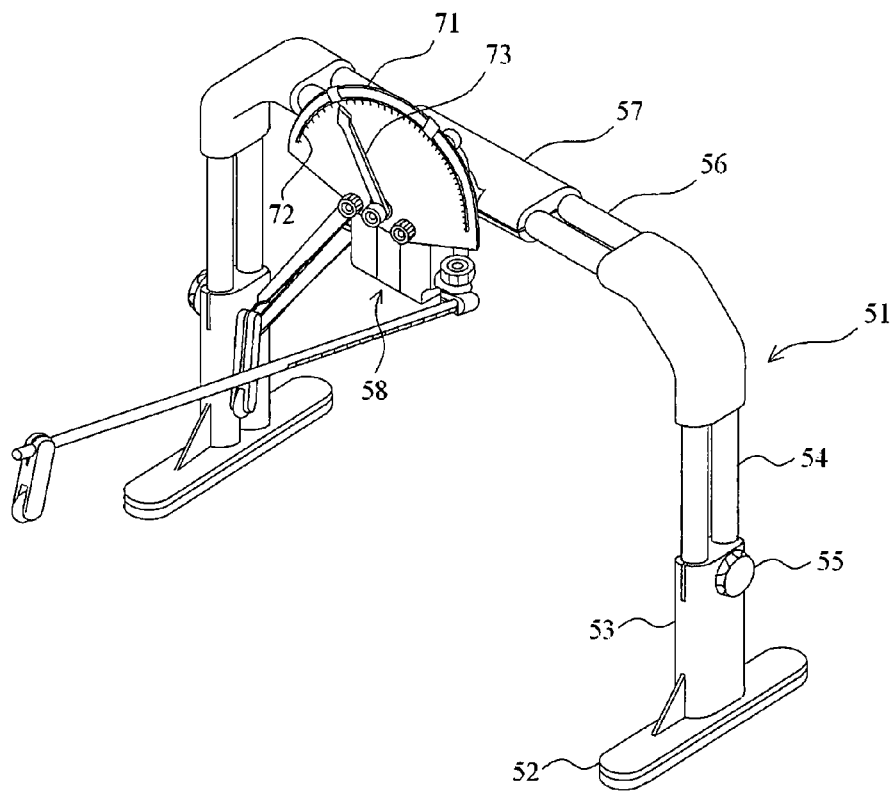
FIG. 8 is a perspective view showing a complete breathing monitoring device having a multi-point detector according to a second embodiment of the present invention.
Figure 9:
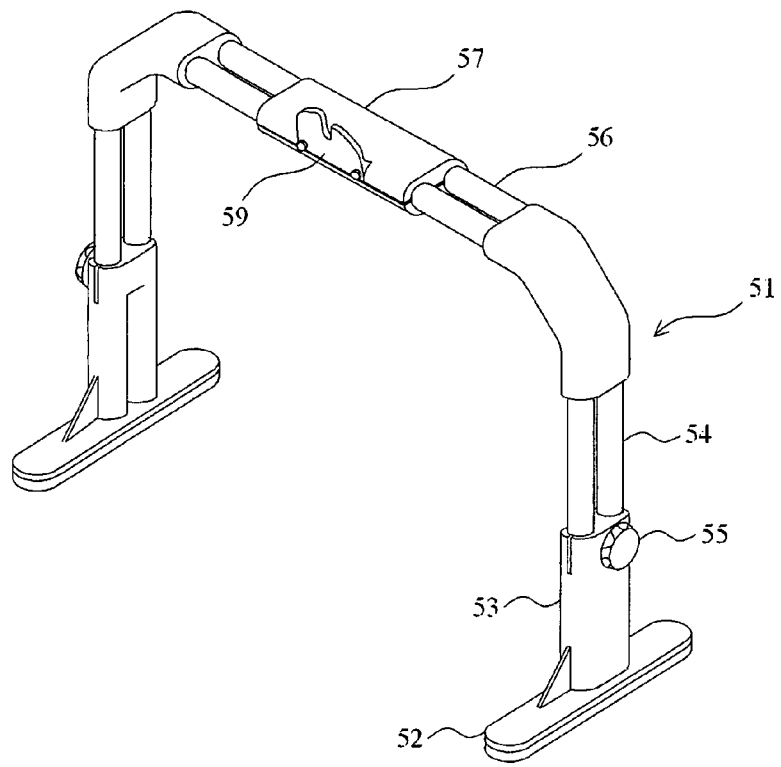
FIG. 9 is a perspective view showing a stand portion of the breathing monitoring device having a multi-point detector.
Figure 10:
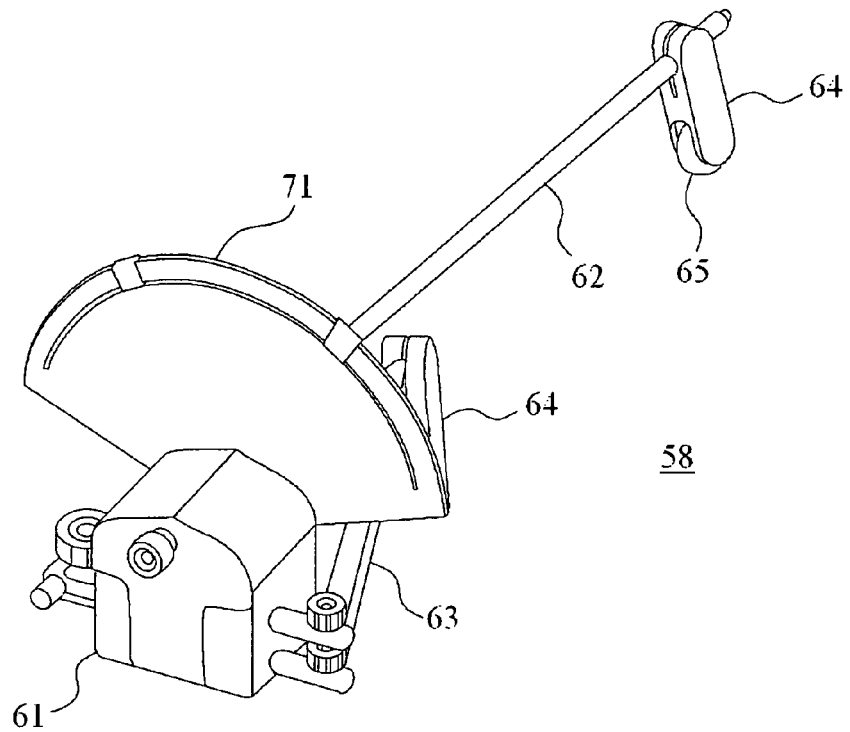
FIG. 10 is a perspective view showing a measurement device.
Figure 11:
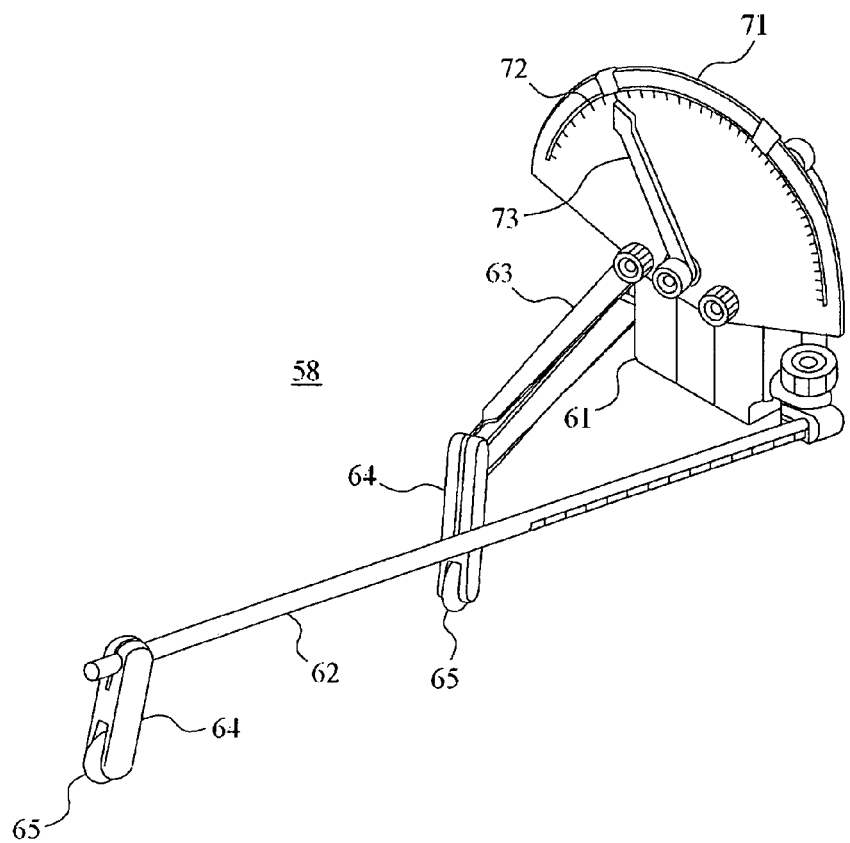
FIG. 11 is a perspective view showing the measurement device shown in FIG. 10, viewed from the other side thereof.

FIG. 8 is a perspective view showing a complete breathing monitoring device having a multi-point detector according to a second embodiment of the present invention; FIG. 9 is a perspective view showing a stand portion thereof; FIG. 10 is a perspective view of a measurement device; and FIG. 11 is a perspective view showing the measurement device shown in FIG. 10, viewed from the other side thereof.

Figure 12:
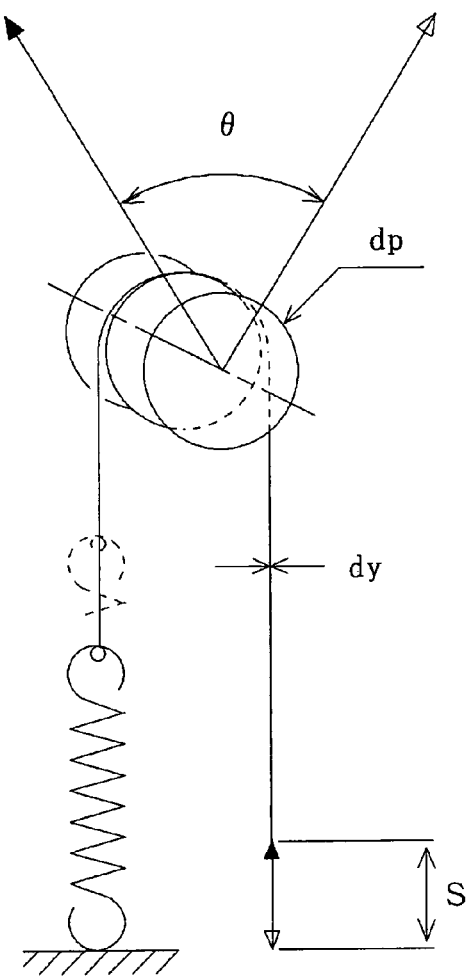
FIG. 12 is a diagram schematically illustrating the operation principle of the measurement device and relation between a string moving amount and an indicator angle.
Figure 13:
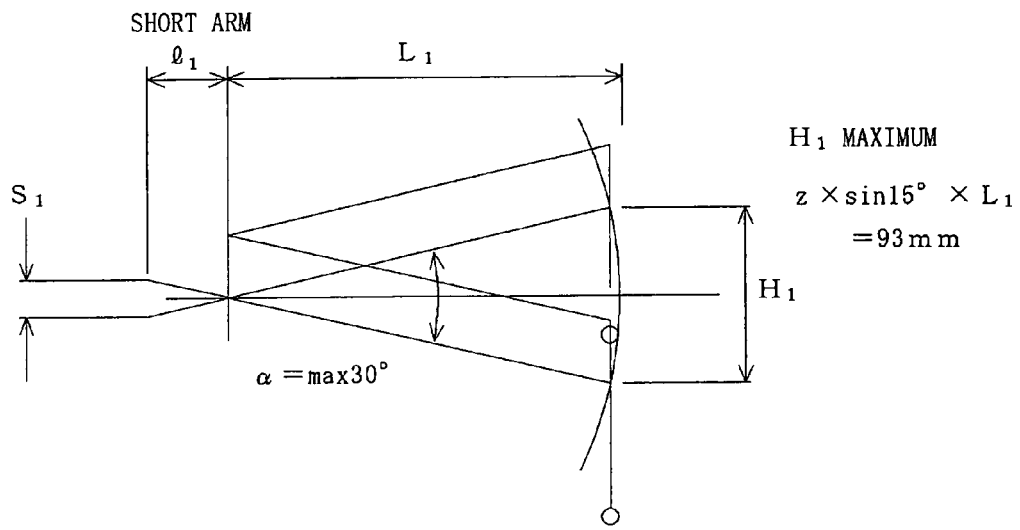
FIG. 13 is a diagram schematically showing a leverage ratio of a short arm of a measurement arm.
Figure 14:
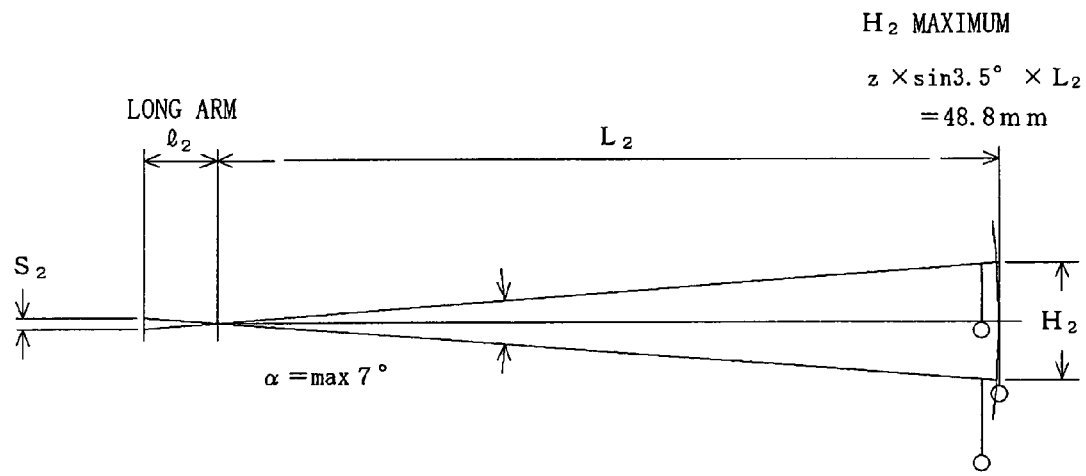
FIG. 14 is a diagram schematically showing a leverage ratio of a long arm of the measurement arm.
Figure 15:
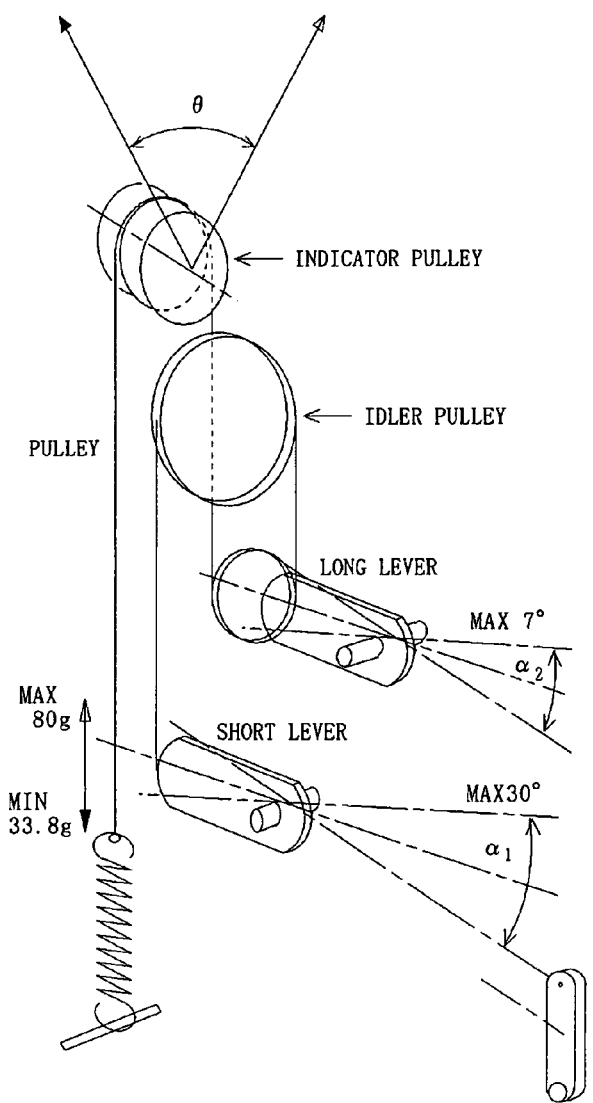
FIG. 15 is a diagram schematically showing a finished measurement arm.

FIGS. 12 to 15 schematically illustrate the operation principle of the measurement device; FIG. 12 is a diagram schematically showing relation between a string moving amount and a indicator angle; FIG. 13 is a diagram schematically showing a leverage ratio of a short arm of a measurement arm; FIG. 14 is a diagram schematically showing a leverage ratio of a long arm of the measurement arm; and FIG. 15 is a diagram schematically showing a finished measurement arm.

In FIGS. 1 to 5, the reference numeral 11 represents a plastic transparent housing, for example, to be mounted to a treatment couch for a patient to lie thereon, so as to cover the chest, abdomen, and so forth of the patient for holding the breathing monitoring device having a multi-point detector according to the present invention above the patient's body, such as the chest, abdomen, and so forth. The housing 11 has a C-like shape opening downward and can change the height thereof relative to the patient by attaching removable legs 12 to the side walls thereof. The reference numeral 13 represents a slide slot formed on the leg 12; 14 represents a height adjustment screw.

The breathing monitoring device having a multi-point detector is mounted on the housing 11. Specifically, a mounting opening 15 where to mount the breathing monitoring device is formed on the top plate of the housing 11, and a C-shaped supporting frame 16 is fixed above so as to cover the mounting opening 15 by means of a mounting screw 17. The supporting frame 16 is also desirably made of transparent plastic. A relatively wide opening 18 is formed in the substantial middle portion of the top plate of the supporting frame 16, which additionally has slide slots 19, 19 formed thereon extending in the length direction on the respective sides of the opening 18.

A position adjustment plate 20 is placed along, so as to intersect, the top plate of the supporting frame 16 and fixed by means of position adjustment screws 21 inserted in the slide slots 19, 19 so as to move in the length direction of the slide slots 19, 19 with the position adjustment screws 21 manipulated. The reference numeral 20-1 represents an angle gauge formed on the tip end surface of the position adjustment plate 20.

An axial bar 22 suspends from the position adjustment plate 20 with a stopper 23 formed at the upper end thereof placed in the opening 18 and the lower end thereof inside the supporting frame 16. A support arm 24 is attached to the lower end of the axial bar 22 so as to rock with the attached point. The support arm 24 axially supports a connection arm 25 at the substantial center thereof with a predetermined interval from the attached point such that the connection arm 25 rocks with the support point. The axially support point of the connection arm 25 desirably has some play.

As shown in FIG. 2, probes 26, 26 are attached to the respective ends of the connection arm 25, extending vertically such that the tips end thereof abut on at least two points on the chest and abdomen regions. The connection arm 25, connecting the probes 26, 26, is retractable via position adjustment screws 29 and auxiliary arms 27 having slide slots 28 formed thereon, so that the connection arm 25 can adjust the length thereof according to the patient's body size or the like.

The probe 26 is dividable into an upper probe 26-1 and a lower probe 26-2. An arrangement in which a male screw 31 at the upper end of the lower probe 26-2 is screwed into a female screw 30 at the lower end of the upper probe 26-1 enables exchange of lower probes 26-2 in various sizes. The reference numeral 32 represents a small screw for use in attaching the probe 26 to the tip end of the auxiliary arm 27.

A displacement amount indicator 33 extends from the attached point in the direction opposite to the support arm 24. The displacement amount indicator 33 has an indicator needle 34 attached to the tip end thereof. In the drawing, the reference numeral 35 represents a balance bar which is an extension of the support arm 24 and provided to keep balanced with the displacement amount indicator 33 to thereby prevent the tip ends of the probes 26, 26 from being excessively loaded.

According to the breathing monitoring device having a multi-point detector of the present invention, the displacement amounts (motion magnitude) of two points on the chest and abdomen of the patient's body are determined using the probes 26, 26, as shown in FIGS. 3 and 4. That is, the probes 26, 26 placed on the chest and abdomen move up or down while keeping in touch with the chest and abdomen according to the patient's body moving due to respiration (see arrows a, b in FIGS. 2 to 4). The up/down movement of the probes 26, 26 placed on the chest and abdomen is transmitted to the connection arm 25, so that the axially support point of the support arm 24 at the center of the connection arm 25 moves up or down according to the combined displacement amount (see the arrow c).

With the axially support point of the support arm 24 moving up or down, the indicator needle 34 provided at the tip of the displacement amount indicator 33 moves accordingly (see the arrow d). Therefore, the combined displacement amount of the support arm 24, or combination of the determined displacement amounts of the probes 26, 26 placed on the chest and abdomen due to respiration, is indicated (shown) by the indicator needle 34 pointing at the scale of the angle gauge 20-1 of the position adjustment plate 20.

It should be noted that the support arm 24 and the displacement amount indicator 33 respectively extend on the opposite sides with the attached point of the support arm 24 in-between. The ratio between the distance l-1 between the attached point of the support arm 24 and the axially support point of the connection arm 25 and the length l-2 of the displacement amount indicator 33 can be desirably determined in consideration of the magnitude of the amplitude of the indicator needle 34, easiness in looking at the moving indicator needle 34, and so forth, and desirably determined as l-1:l-2=about 1:1 to 10.

As shown in FIGS. 6 and 7, the patient looking the indicator needle 34 moving up/down can visually recognize the state of his/her own respiration. In the drawings, the reference numeral 41 represents a press button switch; 42 represents an indicator unit which lights in response to the press button switch 41 pressed. In image capturing or radio-therapy irradiation, the patient is asked to hold the press button switch 41 and, while looking at the indicator needle 34 moving up/down, to press the press button switch 41 in response to the indicator needle 34 pointing at a value within a particular positional range determined for the patient.

With the button switch 41 pressed, the indicator unit 42 lights, upon which the technical staff working in a remote place can know the situation of the patient's respiration. In addition, with a switch signal simultaneously transmitted to an inspection device or a treatment device, respiration-gated technique to control the progress of inspection or that of radio-therapy irradiation in synchronism with the patient's respiration can be carried out.

It should be noted that the angle gauge 20-1 may be placed on the other side of the position adjustment plate 20 from the side mentioned in the above description, which enables the patient to look at the angular gauge 20-1, so that the technical staff engaged in image capturing or radio-therapy irradiation can work accurately while being aware of the state of the patient's respiration by looking at the angular gauge 20-1.

According to the breathing monitoring device having a multi-point detector according to the present invention, the patient can visually recognize the combined displacement amount of his/her body varying due to respiration and thus can exert control by himself/herself such that the combined displacement amount of the patient's body due to respiration remains in a specific range.

EXAMPLE

Method in Use:

Twenty radiation therapy patients (chest:abdomen=13:7, 75 years old on average) were asked to hold self breathing, using a respiration monitoring device having a two-point (chest and abdomen) detector, or the breathing monitoring device having a multi-point detector according to the present invention. The position of a tumor was determined every fluoroscopic imaging. The patient was trained to hold breathing in order to avoid an error larger than 5 mm, and a period of time required to attain the aim is measured. With breathing held, a position marked on the patient's skin was subjected to CT scanning with 2 mm thick to measure reproducibility, or accuracy in reproduction, and also a wider range on the patient's skin including the position where the respiration position measurement device was placed was subjected to CT scanning with 7 mm thick.

Results: (all average values)

1) Three Dimensional Validation in Reproducibility of Tumor Position by CT with Voluntary Breathing Held
   twenty patients, 60 time measurements
   head to toe direction 1.3 mm
   front to back direction 1.6 mm
   right to left direction 1.4 mm 2) Probe Positions on Chest Wall and Abdominal Wall and Three Dimensional Validation in Reproducibility of Tumor Position
   ten patients, 20 time measurements
   maximum positional difference of abdomen probe/respiration-caused moving distance of abdominal wall 5.5 mm/22 mm
   maximum positional difference of chest probe/respiration-caused moving distance of chest wall 3.5 mm/22 mm Review:

The accuracy in three dimensional reproduction of a tumor position, using a CT with voluntary breathing held using the breathing monitoring device having a multi-point detector according to the present invention is of an error within 2 mm. That is, high accuracy is proved. Also, analysis on repeating breathings proves that accuracy in position reproduction using a conventional breathing monitoring device having single point sensing function is of possible displacement by an extent of one fourth to sixth of a respiration-caused moving distance (10 to 40 mm) due to coexisting lung and abdominal breathings. This means that the accuracy in three dimensional reproduction of a tumor position with voluntary breathing held using a breathing monitoring device having a multi-point detector according to the present invention is superior to that using a conventional breathing monitoring device having single point sensing function. This result is similarly applicable even under unstable breathing condition due to coexisting chest and abdominal breathings. A breathing monitoring device having a multi-point detector for simultaneous measurement of two points on the chest and abdomen is not conventionally available and is advantageous as being usable under unstable breathing condition due to coexisting chest and abdominal breathings.

Moreover, a breathing holding method using the breathing monitoring device having a multi-point detector according to the present invention is readily understandable to a patient, which can produce another advantage of a reduced period of time required in successive measurements.

It should be noted that the contact-type determination means having a probe at the tip end thereof, described in the above as displacement amount determination means for determining displacement amounts of at least two points on the chest and abdomen of the patient, of the breathing monitoring device having a multi-point detector according to the present invention, is not an exclusive example, and that, obviously, a non-contact-type determination means using an optical, magnetic, supersonic sensor, or the like, is similarly applicable.

The breathing monitoring device having a multi-point detector according to the present invention may have an electric signal generating mechanism for notifying a technical staff remote treating the patient, when the patient visually recognizes the combined displacement amount of the patient's body due to respiration and recognizes that the combined displacement amount of the patient's body due to respiration stays in the specific range. Such an electric signal generation mechanism may include a monitor, a signal light, and so forth installed near the technical staff treating the patient.

Also, the breathing monitoring device having a multi-point detector according to the present invention may have a signal generating mechanism for generating a synchronizing signal for controlling an inspection device and/or a treatment device so as to suspend or continue an inspection and/or treatment operation when the patient visually recognizes the combined displacement amount of the patient's body due to respiration and recognizes that the combined displacement amount of the patient's body due to respiration stays in the specific range. Such a signal generation mechanism may include an automatic stop switch, an alert device, and so forth installed near the technical staff treating the patient.

FIGS. 8 to 11 show a respiration monitoring device having a multi-point detector according to a second embodiment of the present invention. In FIGS. 8 and 9, the reference numeral 51 represents a stand to be mounted to a treatment couch for a patient to lie thereon, so as to cover the body, such as the chest, abdomen, and so forth, of the patient, for holding the breathing monitoring device having a multi-point detector according to the present invention above the patient's body, such as the chest, abdomen, and so forth. The stand 51 has a C-like shape opening downward, having pedestals 52 adapted to attachment to a treatment couch or the like, on the respective sides thereof. The pedestal 52 has a slide guide 53 standing therefrom. The leg 54 of the C-shaped stand 51 is attached in a removable manner to the slide guide 53, so that the stand 51 can change the height thereof according to the patient. The reference numeral 55 represents a height adjustment screw attached outside the slide guide 53.

A mounting unit 57 for mounting a measurement device 58 is slidably attached to the upper bridge portion 56 of the stand 51, with a bracket 59 for mounting the measurement device 58, attached to the side edge thereof.

In FIGS. 10 and 11, showing the measurement device 58, the reference numeral 61 represents a casing of the measurement device 58. With the casing mounted to the bracket 59 on the side edge of the mounting unit 57, the casing 61 is fixedly mounted to the mounting unit 57.

The casing 61 has a long arm 62 having a probe 64 at the tip end thereof and a short arm 63 having a probe 64 at the tip end thereof, the arms mounted on the respective sides of the casing 61 so as to rotate. The reference numeral 65 represents a roller rotatably mounted at the lower end of the probe 64. The long arm 62 and the short arm 63 are attached to the casing 61 of the measurement device at a predetermined angle so that the respective probes 64 at the tip ends of the arms 62, 63 are placed along the patient's body.

The reference numeral 71 represents a fan-like angle gauge attached to the upper portion of the casing 61 of the measurement device 58, with an angler scale 72 marked along the peripheral arc portion thereof. The reference numeral 73 represents an indicator for pointing at a predetermined angle on the angler scale 72, which is driven by the measurement device 58 according to the movement of the probe 64.

In the following, an operation principle of the measurement device 58 will be described with reference to FIGS. 12 to 15. In FIG. 12, schematically illustrating the relationship between the indicator angle and a string moving amount, in which $\theta$ represents the angle of the indicator, dp represents the radius of an indicator pulley, dy represents a string diameter, and S represents a string moving amount. In the above, the angle $\theta$ of the indicator is obtained by the following expression (1).

[Expression 1]

$$\frac{\theta}{360°} = \frac{S}{\pi(dp + dy)} \quad (1)$$

$$\therefore \theta = \frac{360° + S}{\pi(dp + dy)}$$

Here, a leverage ratio of the measurement arm, which affects the string moving amount S, is considered. In FIG. 13, schematically illustrating the leverage ratio with the short arm of the measurement arm, in which $L_1$ represents a short arm length, $L_2$ represents a long arm length, $l_1$ represents a short arm lever length, $l_2$ represents a long arm lever length, $H_1$ represents a short arm measurement height, $H_2$ represents a long arm measurement height, $S_1$ represents a short arm lever moving amount, and $S_2$ represents a long arm lever moving amount. In the above, the short arm lever moving amount $S_1$ is obtained by the following expression (2).

[Expression 2]

$$S_1 = \frac{H_1 + \ell_1}{L_1} \quad (2)$$

In FIG. 14, illustrating the leverage ratio with the long arm of the measurement arm, the long arm lever moving amount $S_2$ is obtained by the following expression (3).

[Expression 3]

$$S_2 = \frac{H_2 + \ell_2}{L_2} \quad (3)$$

However, in obtaining the string moving amount S, a structure satisfying the following condition is indispensable.

(1) displayed value is the total value of both probe heights (a moving amount); and (2) the ratio between a measurement height (input) and displayed value (output) is the same for both arms.

The values of S for the short and long arms are calculated in FIG. 15 (see FIGS. 13 and 14). With the expressions (2) and (3), the values of S with the measurement height being 10 mm are obtained by the following expressions (4) and (5).

[Expression 4]

$$S_1 = \frac{H_1 + \ell_1}{L_1} = \frac{10 + 30}{180} = 1.667 \, mm \quad (4)$$

[Expression 5]

$$S_2 = \frac{H_2 + \ell_2}{L_2} = \frac{10 \times 30}{360} = 0.833 \, mm \quad (5)$$

In the above, the condition (2) is not satisfied as S1/S2=0.5. In order to satisfy the condition (2), S1=2×S2 needs to be held. Then, by providing a pulley at a point corresponding to the lever length on the long arm side, as shown in FIG. 15, the value of $S_2$ can be doubled (note: the long arm length is variable depending on the setting, with the value $S_2$ thus slightly variable). It should be noted that there is only a single string used, the string moving amount S to be transmitted to the indicator pulley is the total of both probes, which satisfies the another condition.

In view of the above, the resolution (measurement height <-> indicator angle) of the device is as follows. That is, with the expressions (1), (2), and (3), the indicator angle for every measurement height 10 mm is obtained by the following expression (6).

[Expression 6]

$$\theta = \frac{360 \cdot S}{\pi (dp + dy)} = \frac{360 \times 1.667}{\pi (8.2 + 0.3)} \approx 22.5° \, (4.5 \times 5 \, scales) \quad (6)$$

In the following, a manner of using the breathing monitoring device having a multi-point detector according to the second embodiment of the present invention will be described.

(1) the leg 54 of the bridge portion 56 is assembled into the slide guide 53 of the pedestal 52 which constitutes the stand 51 and fixed at a predetermined position by the height adjustment screw 55 (see FIGS. 8 and 9);

(2) the angle gauge 71 and the indicator 73 are mounted to the casing 61 of the measurement device and fixed by a screw (see FIGS. 10 and 11);

(3) the long arm 62 and the short arm 63, both having the probes 64, are mounted to the measurement device 58 (see FIGS. 10 and 11);

(4) the finished measurement device 58 is assembled to the stand 51;

(5) a patient is asked to lie on the treatment couch, and a patient mirror (not shown) is attached in a position such that the lying patient can look at the monitor indicator 73 of the breathing monitoring device;

(6) the probe 64 is placed in the reference position, and the position, height, width, and so forth of the breathing monitoring device are adjusted;

(7) the patient is asked, while looking at the moving monitor indicator 73 to thereby know the movement of his/her body surface due to respiration, to adjust his/her own respiration such that the monitor indicator 73 presents a stable amplitude and finally stays in a particular position; and (8) with the indicator 73 staying in a particular position, CT scanning, MR scanning, or irradiation is carried out.

The present invention is applicable not only to a case in which an image capturing or radio-therapy irradiation is applied using a CT (computer tomography system) device or a radio therapy system, but also to various inspections, treatments, and so forth which require so-called respiratory-gated operation in which the moving amount of a patient is determined and image capturing and radio-therapy irradiation is carried out in synchronism with the body movement.

What is claimed is:

1. A breathing monitoring device having a multi-point detector, comprising:
    a housing mounted to a treatment couch for a patient to lie thereon, the housing covering the patient's body including a chest or an abdomen;
    displacement amount determination means mounted to the housing, for determining displacement amounts of at least a point on the patient's chest and a point of the patient's abdomen, includes a contact-type determination means having
      probes for abutting at least two points on the chest and the abdomen, respectively,
      a connection arm connecting the probes,
      a support arm for supporting the connection arm at a center thereof so as to rock, and
      a displacement amount indicator extending from an axially attached point of the support arm in a direction opposite the support arm; and
    respiration level determination means for determining a combined displacement amount that is a combination of the determined displacement amounts of the patient's chest and abdomen due to respiration.

2. The breathing monitoring device having a multi-point detector according to claim 1, wherein the displacement amount determination means is disposed to be visually accessible to the patient so that the patient can visually recognize the combined displacement amount of the patient's body due to respiration, and control himself/herself such that the combined displacement amount of the patient's body due to respiration stays in a specific range.

3. The breathing monitoring device having a multi-point detector according to claim 2, further comprising:
    an electric signal generation mechanism for notifying a technical staff remotely treating the patient when the patient visually recognizes the combined displacement amount of the patient's body due to respiration.

4. The breathing monitoring device having a multi-point detector according to claim 2, further comprising a signal generation mechanism for generating a synchronizing signal for controlling at least one of an inspection device and a treatment device so as to suspend or continue at least one of an inspection and treatment operation when the patient visually recognizes the combined displacement amount of the patient's body due to respiration.

5. A breathing monitoring device having a multi-point detector, comprising:
- a housing mounted to a treatment couch for a patient to lie thereon, the housing covering the patient's body including a chest and abdomen;
- displacement amount determination means mounted to the housing, for determining displacement amounts of at least a point on the patient's chest and a point on the patient's abdomen, emen using a contact-type determination means having
  - two probes for abutting at least two points on the chest and the abdomen, respectively, and
  - one long arm and one short arm for respectively supporting the probes, wherein an operation of each of the arms is transformed into an angular change of a displacement amount indicator by utilizing a pulley and a wire; and
- respiration level determination means for determining a combined displacement amount that is a combination of the determined displacement amounts of the patient's chest and abdomen due to respiration.

6. The breathing monitoring device having a multi-point detector according to claim 5, wherein the displacement amount determination means is disposed to be visually accessible to the patient so that the patient can visually recognize the combined displacement amount of the patient's body due to respiration, and control himself/herself such that the combined displacement amount of the patient's body due to respiration stays in a specific range.

7. The breathing monitoring device having a multi-point detector according to claim 6, further comprising:
- an electric signal generation mechanism for notifying a technical staff remotely treating the patient when the patient visually recognizes the combined displacement amount of the patient's body due to respiration.

8. The breathing monitoring device having a multi-point detector according to claim 6, further comprising:
- a signal generation mechanism for generating a synchronizing signal for controlling at least one of an inspection device and a treatment device so as to suspend or continue at least one of an inspection and treatment operation when the patient visually recognizes the combined displacement amount of the patient's body due to respiration.

* * * * *